(12) United States Patent
Lee et al.

(10) Patent No.: US 11,460,920 B2
(45) Date of Patent: Oct. 4, 2022

(54) FREQUENCY INFORMATION-BASED COMPUTER HAVING SENSOR INTERFACE

(71) Applicant: DAEGU GYEONGBUK INSTITUTE OF SCIENCE AND TECHNOLOGY, Daegu (KR)

(72) Inventors: Sang Cheol Lee, Daegu (KR); Woo Young Jung, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 692 days.

(21) Appl. No.: 16/472,345

(22) PCT Filed: Dec. 8, 2017

(86) PCT No.: PCT/KR2017/014372
§ 371 (c)(1),
(2) Date: Jun. 21, 2019

(87) PCT Pub. No.: WO2018/117502
PCT Pub. Date: Jun. 28, 2018

(65) Prior Publication Data
US 2019/0377411 A1    Dec. 12, 2019

(30) Foreign Application Priority Data

Dec. 23, 2016 (KR) .................. 10-2016-0177519

(51) Int. Cl.
*G06F 3/01* (2006.01)
*A61B 5/00* (2006.01)
(Continued)

(52) U.S. Cl.
CPC .............. *G06F 3/015* (2013.01); *A61B 5/374* (2021.01); *A61B 5/7267* (2013.01); *H03H 9/14502* (2013.01)

(58) Field of Classification Search
CPC ....... G06F 3/015; A61B 5/374; A61B 5/7267; H03H 9/14502
See application file for complete search history.

(56) References Cited

U.S. PATENT DOCUMENTS

| | | | | |
|---|---|---|---|---|
| 2011/0242001 | A1* | 10/2011 | Zhang | G06F 3/044 345/173 |
| 2013/0201316 | A1* | 8/2013 | Binder | H04L 67/12 701/2 |
| 2014/0247230 | A1* | 9/2014 | Sheng | G06F 3/0436 345/173 |

FOREIGN PATENT DOCUMENTS

| | | |
|---|---|---|
| JP | H-03196251 | 8/1991 |
| KR | 10-2009-0038170 | 4/2009 |

(Continued)

OTHER PUBLICATIONS

International Search Report issued by the Korean Intellectual Property Office acting as the International Searching Authority in relation to International Application No. PCT/KR2017/014372 dated Mar. 29, 2018 along with English language translation (5 pages).

*Primary Examiner* — Robert J Michaud
(74) *Attorney, Agent, or Firm* — Harness, Dickey & Pierce, P.L.C.

(57) ABSTRACT

A hybrid wave computer that computes an inputted original signal as frequency information includes: an input module configured to separate a frequency of the original signal by detecting an oscillation of an piezoelectric element by each position as the original signal having an embedded frequency of several bands is transmitted in a form of acoustic waves on a substrate provided with the piezoelectric element; a calculation module including at least one vibration amplifier or vibration damper for receiving the frequency of the original signal separated in the input module and amplifying or attenuating a wave for each frequency band to (Continued)

calculate the inputted original signal in a frequency band; and a storage module configured to store binarized frequency information in the calculation module as digital information, so that the original signal is interfaced in a form of waves.

8 Claims, 4 Drawing Sheets

(51) Int. Cl.
*H03H 9/145* (2006.01)
*A61B 5/374* (2021.01)

(56) References Cited

FOREIGN PATENT DOCUMENTS

| | | |
|---|---|---|
| KR | 10-1387672 | 4/2014 |
| KR | 10-1457477 | 11/2014 |
| KR | 10-2016-0144655 | 12/2016 |

\* cited by examiner

FREQUENCY INFORMATION-BASED COMPUTER HAVING SENSOR INTERFACE

CROSS-REFERENCE TO RELATED APPLICATIONS

This application is a national phase entry under 35 U.S.C. 371 of PCT International Application No. PCT/KR2017/014372 filed Dec. 8, 2017, which claims priority to Korean Patent Application No. 10-2016-0177519, filed Dec. 23, 2016, the disclosure of each of these applications is expressly incorporated herein by reference in their entirety.

TECHNICAL FIELD

The present invention relates to a frequency information-based computer having a sensor interface.

Specifically, the present invention relates to a computer that provides a new interface compatible with a digital computer by calculating frequency information of an input signal.

BACKGROUND INFORMATION

Computers are also called electronic calculators. There are analog and digital types in computers, but analog type is rarely used since the 1960s. In the early 19th century, a British mathematician C. Babbage planned a machine that automatically performs calculations while decoding a series of instructions for programming on computers today. The first machine to automatically perform calculations was completed in 1944 with the relay calculator MARK-I, led by H. H. Aiken of Harvard University. The first successful electronic calculator, that is, a calculator using a vacuum tube, is ENIAC made by J. W. Moccleigh and J. P. Eckert of the University of Pennsylvania around 1945.

On the other hand, in 1946 J. L. Neumann proposed the so-called built-in method of storing computer instructions and numerical values together in the memory device like the present computer, and it is the basic principle of computers today.

The first commercial computer is the UNIVAC-I from Sperry Land. UNIVAC-I used magnetic tapes as input/output devices. If the development process of the computer in terms of hardware is divided into several generations ever since commercial computers began to be used, the first generation is a computer with a vacuum tube as its main element from 1950 to 1956 to 1957, the second generation is a computer using semiconductor devices such as transistors and diodes from around 1957 to around 1964, the third generation is a computer using integrated circuits from around 1965 to the mid 1970s, and the fourth generation computer uses high-density integrated circuits from around 1975 to the last.

The fifth generation computer project has been under research and development for a decade since 1982. The period of research and development is divided into early 3 years, mid 4 years, and late 3 years. Research and development is conducted by the New Generation Computer Technology Development Organization (ICOT) as a commissioned study by the Ministry of Industry. Early research and development focuses on the development of basic technology necessary to build the fifth generation computer. In the mid-term, it developed subsystems that are the basis of fifth-generation computers. In the latter period, it aims to complete the final prototype for the fifth generation computer by integrating the research and development achievements so far.

While the fifth-generation computer is aimed at a left-brain computer corresponding to a human logical judgment function, the sixth generation computer refers to a computer that is responsible for the right brain part that carries out figure recognition and intuition. The sixth generation computer is currently in development, and the development of the right brain type computer fuses neural circuit computers that imitate the mechanism of information processing with the human brain or technologies such as super parallel computers and ultra-distributed computers that share and process large amounts of information.

Korean Patent No. 1457477 (hereinafter abbreviated as "prior art") relates to a computer employing an extended interface such as a sixth generation computer, and discloses 'a brain-wave inducing device, brain computer interface system and method using auditory stimulation'. Prior art documents disclose a computer system that generates auditory stimulation signals using carrier signals and message signals, which are sounds of music or nature, and receives and analyzes user's brain waves in response to the signals. In other words, the prior art discloses a system in which a human brain wave formed by a neuron association constituting the brain is converted into a digital signal and converted or calculated into a digital computer instruction.

However, in the process of using a digital computer, information may be lost because the analog information of the physical space is transmitted or connected to the virtual space through the conversion process. Therefore, there is an increasing interest in computers with new types of interfaces to prevent the loss of these conversion processes.

Until now, digital computers have only passively received information inputted from sensors such as a keyboard, a mouse, and the like, so that there is a fundamental limitation in recognizing external information. Especially, sensor interface in the Internet of Things technology still requires much efforts to overcome the problems such as power consumption, size and reliability, and in the era of cyber physical systems or systems of system, it is concerned that digital bottlenecks, which are bottlenecks in information links with the physical world, will occur.

Accordingly, Applicant has devised a model capable of a wave-type input interface that has an excellent analog input function and is able to fully utilize digital calculation capability, as a model of a future computer.

(Patent literature 1) Korean Patent No. 1457477

DISCLOSURE OF THE INVENTION

Technical Problem

It is an object of the present invention to provide a computer that receives analog signals such as light, waves, and vibrations and is interfaced in the form of waves to overcome limitations of passive information recognition and digital signal processing, and more specifically, to provide a new type of computer capable of performing analog interface and digital calculations.

Technical Solution

In order to achieve the above object, according to the present invention, in a hybrid wave computer that computes an inputted original signal as frequency information, the hybrid wave computer includes: an input module configured to separate a frequency of the original signal by detecting an oscillation of an piezoelectric element by each position as the original signal having an embedded frequency of several bands is transmitted in a form of acoustic waves on a substrate provided with the piezoelectric element; a calculation module including at least one vibration amplifier or vibration damper for receiving the frequency of the original signal separated in the input module and amplifying or attenuating a wave for each frequency band to calculate the inputted original signal in a frequency band; and a storage module configured to store binarized frequency information in the calculation module as digital information, so that the original signal is interfaced in a form of waves.

Preferably, the hybrid wave computer may further include a sensor unit configured to oscillate the input module in response to an external environment.

Preferably, the input module may include a piezoelectric substrate for receiving the original signal and converting the received original signal into a surface acoustic wave, wherein the piezoelectric substrate may have a metal line formed on a surface thereof in a direction perpendicular to a direction in which the surface acoustic wave advances.

Preferably, in the piezoelectric substrate, a plurality of the metal lines may be arranged at regular intervals, and the metal lines may be formed in an arrangement in which fixed ends are crossed in a vertical direction.

Preferably, the input module may further include an electrode port for outputting each separate frequency, wherein the electrode port may be disposed in each area of the fixed end.

Preferably, the calculation module may include: a compression sensing unit configured to sample a magnitude of a signal for each separated frequency band of the original signal; and a digital conversion unit configured to binarize a magnitude of a signal sampled in the compression sensing unit to convert the binarized magnitude into a digital signal, wherein the compression sensing unit may sample a signal with a value less than twice the highest frequency of the signal for each separated frequency band of the original signal.

Preferably, the calculation module may further include a processor having an artificial neural network algorithm embedded therein, wherein the processor may receive a magnitude of a signal for each frequency band of the original signal outputted from the digital conversion unit and generate output information through machine learning.

Preferably, the storage module may divide the binarized frequency information by each frequency band and store the divided binarized frequency information.

Advantageous Effects

The present invention implements a physical virtual space full connection interfeel platform, which includes a sensor unit that responds to information with frequency components and an input module that is capable of calculating the wave based on the frequency component against discrete calculation using the information received from the sensor unit.

According to the present invention, by using the attenuation characteristics of the surface acoustic waves, the analog signal is separated into the input modules by frequency band, and the calculation necessary for interface is performed using the frequency band signal as the input value, so that information is calculated in the frequency band without a separate Fourier transform process. In addition, since the information of each frequency band signal is stored in the storage module as digital data, it may be linked with algorithms such as artificial neural networks.

Accordingly, the present invention is advantageous in that the analog input function is enhanced in addition to processing of existing user input or single sensor information, and information processing in which a human sense organ or brain is simulated may be performed.

DETAILED DESCRIPTION

Figure 1:
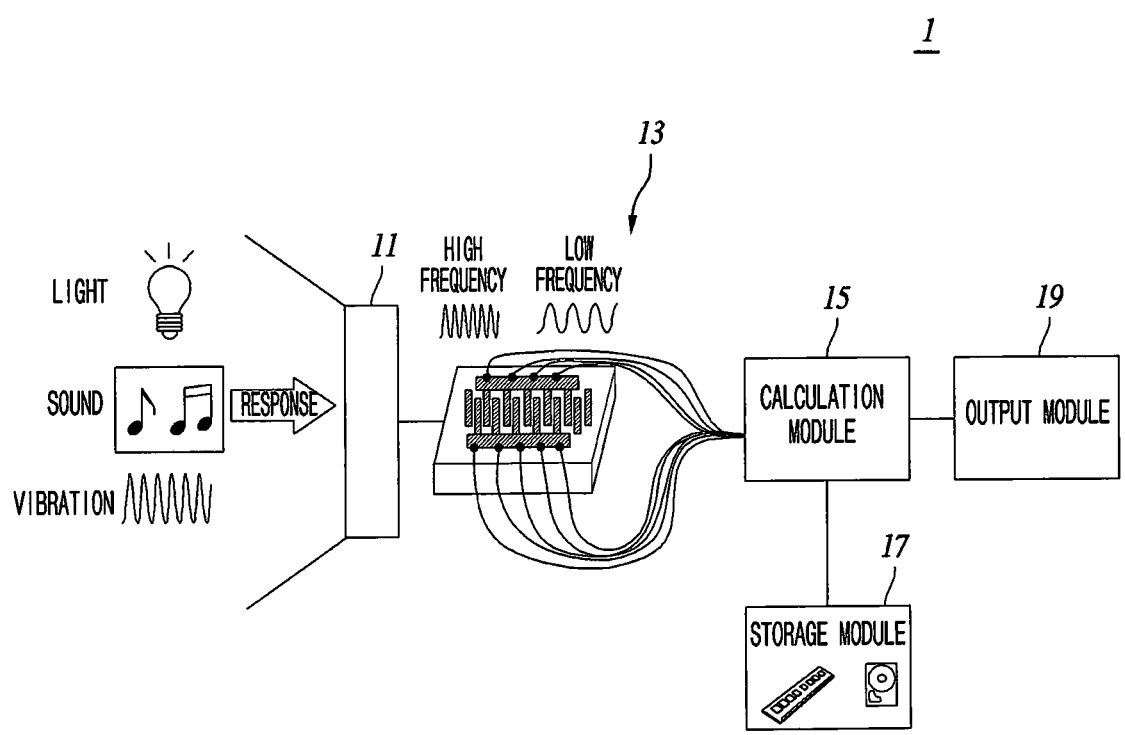
FIG. 1 is a hybrid wave computer according to an embodiment of the present invention.

Hereinafter, the present invention will be described in more detail with reference to the contents described in the accompanying drawings. However, the present invention is not limited or restricted to exemplary embodiments. Like reference numerals in each drawing represent members for performing the same function substantially.

The objects and effects of the present invention may be understood or clarified naturally by the following description, and the purpose and effect of the present invention are not limited by the following description. In addition, in describing the present invention, when it is determined that the detailed description of known technology related to the present invention may unnecessarily obscure the essential point of the present invention, a detailed description thereof will be omitted.

In this specification, the hybrid wave computer 1 was used to illustrate one embodiment of a computer using future computer technology. Unlike digital signals that are received passively from the input devices of existing computers, the hybrid wave computer 1 is a computer that receives external signals in the form of waves, and performs a process of informationizing and recognizing the external signals. In addition, the hybrid wave computer 1 may interface the inputted analog signal in the region of the wave, or may be compatible with the various algorithms of digital computers that are currently available in conjunction with digital signal processing.

FIG. 1 is a hybrid wave computer 1 according to an embodiment of the present invention. Referring to FIG. 1, the hybrid wave computer 1 may include a sensor unit 11, an input module 13, a calculation module 15, a storage module 17, and an output module 19. The hybrid wave computer 1 according to the embodiment of the present invention may implement a physical-virtual space interface in which information is exchanged with frequency components. In other words, the hybrid wave computer 1 may calculate the inputted original signal 3 as frequency information. In addition, in the hybrid wave computer 1, the inputted original signal 3 may be interfaced in the form of waves. Hereinafter, each configuration of the hybrid wave computer 1 according to the present embodiment will be described in detail.

The sensor unit 11 may oscillate the input module 13 in response to the external environment.

In this embodiment, the sensor unit 11 may respond to all the stimulation having the characteristics of waves such as light, sound, vibration and the like. The sensor unit 11 may be provided with different sensor elements depending on the type of stimulation. In this embodiment, when it is to receive light information with an analog input interface, a photodiode may be used, and when it is to receive vibration information of sound or other objects, acoustic sensors or piezoelectric sensors may be used. The sensor unit 11 may be understood as an input device for obtaining a desired analog according to the purpose of the hybrid wave computer 1. The sensor unit 11 may transmit the inputted stimulation to the input module 13 to oscillate the input module 13.

As in the present embodiment, the input interface of the hybrid wave computer 1 may prevent loss of data by eliminating the conversion process in the process of responding to external stimulation.

Figure 2:
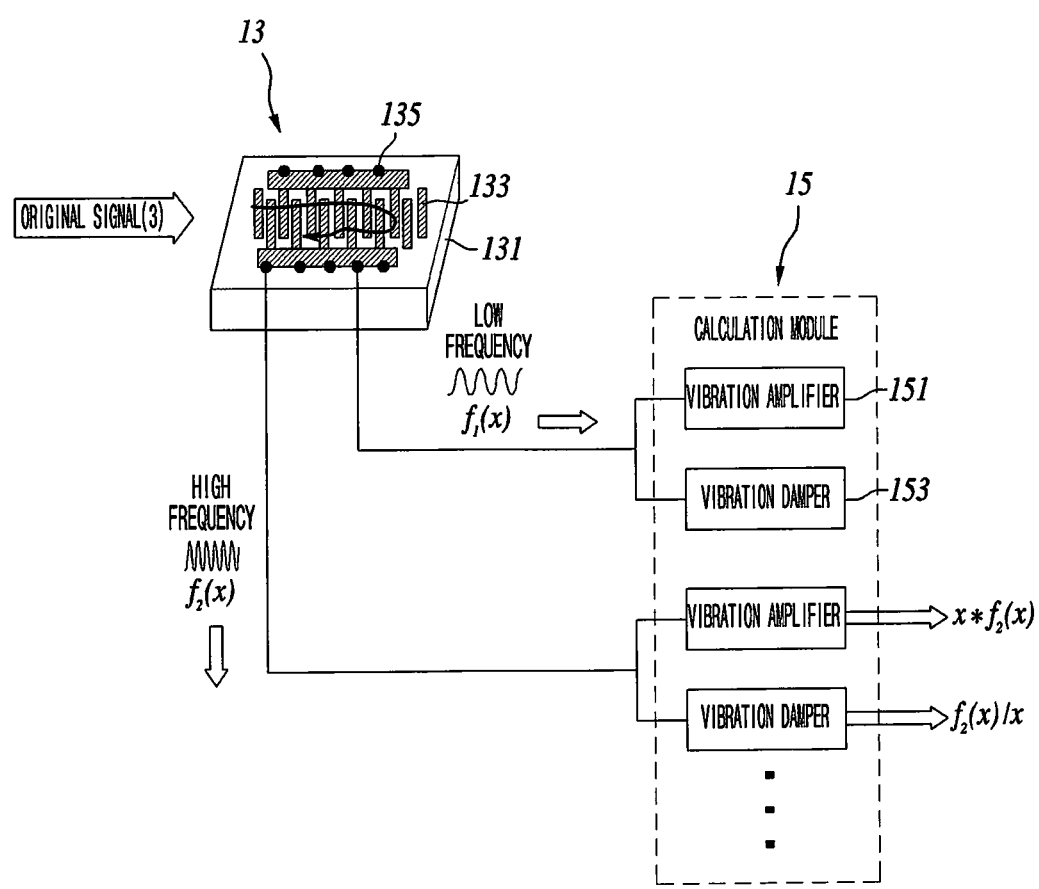
FIG. 2 shows a processing procedure of an original signal according to an embodiment of the present invention.

FIG. 2 shows a processing procedure of an original signal 3 according to an embodiment of the present invention. Referring to FIG. 2, the input module 13 may include a piezoelectric substrate 131, a metal line 133, and an electrode port 135.

The original signal 3 refers to a signal received by the sensor unit 11 and outputted to the input module 13. The original signal 3 may be various signal information in analog form such as a light signal, a sound signal, and a vibration signal according to the embodiment of the sensor unit 11, and may be a signal in which frequencies of various bands are embedded.

The original signal 3, in which the frequencies of several bands are embedded, is transmitted in the form of acoustic waves on a substrate provided with a piezoelectric element, so that by detecting the oscillation of the piezoelectric element by position, the input module 13 may separate the frequency of the original signal 3.

In this embodiment, the input module 13 may transmit the original signal 3 received from the sensor unit 11 in the form of a surface acoustic wave.

A surface acoustic wave represents the state of a wave transmitted along the surface of a substrate. The surface acoustic wave has a characteristic of being rapidly attenuated in the depth direction. The input module 13 according to the present embodiment may be implemented as a frequency selective functional element, and in this case, when a metal electrode is formed on a substrate having a large insulating property and a piezoelectric is applied, the surface of the substrate is temporarily twisted to cause a physical wave.

As a one-port resonator having reflectors disposed on both sides thereof is configured in parallel with a comb-shaped transducer that converts from an electric system to an acoustic system, which is a wave form, or from an acoustic system to an electric system, the input module 13 according to the present embodiment may be provided in a ladder form so as to filter or extract a certain frequency band. The comb-shaped transducer may be an interdigital transducer (IDT) as an example.

In relation to the input module 13, in the process of transmitting surface acoustic waves, as the Inside of the medium where the acoustic wave penetrates has a higher frequency, energy loss increases, and accordingly, the attenuation resulting therefrom may be increased. Therefore, the penetration depth for the frequency and the medium may be inversely proportional. That is, the high frequency penetrates the short distance, and the low frequency penetrates the long distance, and the input module 13 may separate frequencies by characteristics according to the penetration distance of the surface acoustic wave of the original signal 3 using these damping characteristics.

The input module 13 may include a piezoelectric substrate 131 for converting the original signal 3 into a surface acoustic wave.

In this embodiment, the input module 13 may receive the original signal 3 and may convert it into a surface acoustic wave. The input module 13 may transmit surface acoustic waves through the piezoelectric substrate 131. The input module 13 may separate the surface acoustic wave according to the penetration depth. The input module 13 may transmit the separated surface acoustic waves to the calculation module 15. The input module 13 may transmit the separated frequency signal to the calculation module 15 in the form of vibration or to the calculation module 15 in the form of an electrical signal according to the vibration of the separated frequency. The number and type of means for connecting the input module 13 and the calculation module 15 are not limited and may be changed flexibly according to the needs of the user.

In this embodiment, the piezoelectric substrate 131 may be provided in any form capable of forming a path in the direction in which the surface acoustic wave advances. In one embodiment, the piezoelectric substrate 131 may be provided in a rectangular parallelepiped form. Also, it is preferable that the surface acoustic wave has an elongated structure in which a long path is formed in consideration of the difference in penetration depth by frequency. For this, the piezoelectric substrate 131 may be implemented in a rolled shape of 'u'.

A metal line 133 may be formed on the surface of the piezoelectric substrate 131 perpendicular to the direction in which the surface acoustic wave advances. In this embodiment, the piezoelectric substrate 131 may be formed with a metal line 133 to convert the stimulation by the pressure during the progression of the surface acoustic wave into an electrical signal.

In this embodiment, in relation to the piezoelectric substrate 131, a plurality of metal lines 133 may be spaced apart at regular intervals in the progressing direction of the surface acoustic wave. The metal lines 133 arranged at regular intervals in the piezoelectric substrate 131 may sense surface acoustic waves passing through the metal lines.

In this embodiment, in relation to the piezoelectric substrate 131, by using the characteristic that the rate at which sound waves attenuate with frequency is different, that is, the characteristic that the penetration depth is different according to frequency, when the metal coating line 133 of the piezoelectric material is arranged at regular intervals in the progressing direction on the substrate, which is the medium through which the surface acoustic wave is transmitted, the sum of the frequencies of the signals received by the metal line 133, which converts into electrical signals at the corresponding depths, differs for each line position.

Through this, the piezoelectric substrate 131 matches characteristics of each position of the plurality of metal lines 133 and frequency characteristics of each wavelength included in the surface acoustic waves to separate surface acoustic waves. That is, referring again to FIG. 2, the piezoelectric substrate 131 may separate the high frequency $f_2(x)$ from the point where the original signal 3 is inputted and the point where the original signal 3 is not separated. On the other hand, the piezoelectric substrate 131 may relatively separate the low frequency $f_1(x)$ at a point separated from the point where the original signal 3 is inputted.

The metal lines 133 may be formed in an arrangement in which fixed ends are crossed in the vertical direction. In this embodiment, the metal lines 133 are formed in a ladder structure arranged to face each other. At this time, it is also understood that the metal lines 133 are alternately arranged on both sides and the fixed end referred to in this specification is defined as a starting point in which the metal line 133 is arranged so as to face each other from the outside of the substrate toward the other metal line.

In this embodiment, a plurality of metal lines 133 arranged perpendicular to the progressing direction of the surface acoustic wave have fixed one ends, and each of the metal lines 133 arranged in series may be arranged such that the fixed ends cross over the piezoelectric substrate 131 vertically.

The electrode port 135 may output each separated frequency and may be disposed in the region of the fixed end of the metal line 133.

The electrode port 135 may be provided as a device for transmitting an electric signal transmitted from the metal line 133 through the stimulation of the surface acoustic wave to the calculation module 15. The electrode port 135 may be disposed at a fixed end of a plurality of metal lines 133 and may transmit an electrical signal transmitted from a surface acoustic wave having different frequency characteristics to the calculation module 15. The shape and the number of the electrode ports 135 are not limited and may be changed according to the needs of the user.

The electrode port 135 may be a means for transmitting an acoustic wave progressing in the metal line 133 in the form of vibration, and may be a conductor that transmits the current signals obtained by converting the acoustic waves progressing in the metal line 133 into electrical signals.

The calculation module 15 includes at least one vibration amplifier 151 or vibration damper 153 for receiving the frequency of the original signal 3 separated from the input module 13 and for amplifying or attenuating the wave in each frequency band so that it may calculate the received original signal 3 in the frequency band.

In this embodiment, the calculation module 15 may be connected to the electrode port 135 of the input module 13 to receive the separated frequency information. The calculation module 15 may include the same number of vibration amplifiers 151 and vibration damper 153. The calculation module 15 may calculate the separated frequencies through the vibration amplifier 151 and the vibration damper 153, respectively. The calculation module 15 may transmit the calculated frequency to the storage module 17 or the output module 19.

According to the present embodiment, the vibration amplifier 151 may amplify each frequency separated from the surface acoustic wave. The plurality of vibration amplifiers 151 may amplify a plurality of frequencies inputted in multiple lines simultaneously. The frequency calculated through the vibration amplifier 151 may be transmitted to the storage module 17 or the output module 19.

The vibration damper 153 may attenuate the respective frequencies separated from the surface acoustic wave. The vibration damper 153 may be provided in plurality to simultaneously attenuate a plurality of frequencies inputted to multiple lines. The frequency calculated through the vibration damper 153 may be transmitted to the storage module 17 or the output module 19.

In this embodiment, it is noticed that the calculation module 15 calculates the input signal in the domain of frequency. With the above feature, the calculation module 15 discriminates the original signal 3 in each frequency band and performs signal processing. Accordingly, the calculation module 15 may be required to have a plurality of vibration amplifiers 151 or vibration dampers 153 for each frequency band.

In this embodiment, the original signal 3 may be separated into a high frequency band signal $f_2(x)$ and a signal $f_1(x)$ in a low frequency band through the input module 13. The separated signal may be amplified or attenuated or arithmetically calculated depending on the type of operation desired. As an example, the signal $f_2(x)$ separated by high frequency may be signal processed in the form of $x*f_2(x)$ or $x*f_2(x)$ according to the calculation of amplification or attenuation in the calculation module.

Figure 3:
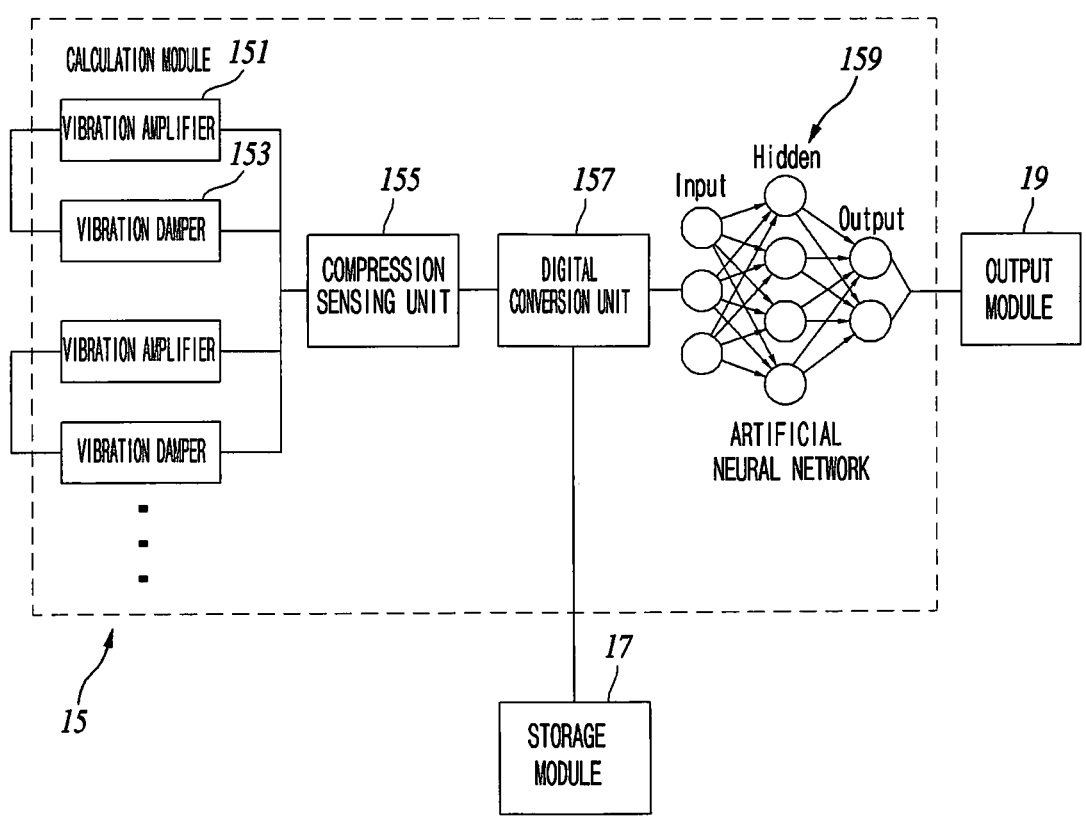
FIG. 3 shows a calculation module and a storage module according to an embodiment of the present invention.

FIG. 3 shows a calculation module 15 and a storage module 17 according to another embodiment of the present invention. Referring to FIG. 3, the calculation module 15 may be associated with a processor having an algorithm embedded therein, such as an artificial neural network 159. In this embodiment, the calculation module 15 may include a compression sensing unit 155, a digital conversion unit 157, and a processor (not shown).

The compression sensing unit 155 may sample the magnitude of the signal for each of the separated frequency bands of the original signal 3. More specifically, the compression sensing unit 155 may sample the signal with a value less than twice the highest frequency of the signal for each of the separated frequency bands of the original signal 3.

The process of converting a natural signal such as an analog signal into a digital signal is performed by a device called an analog-to-digital converter (ADC) incorporated in the digital conversion unit 157. These ADC devices have been built on the basis of the Shannon-Nyquist sampling theory that samples must be sampled more than twice the highest frequency of the signal to restore the signal back to the analog signal correctly.

In this embodiment, the rate at which the compression sensing unit 155 samples is proportional to the amount of information that may be represented. On the other hand, in this embodiment, even though the process of sampling arbitrary signals through the configuration of the compression sensing unit 155 proceeds slowly, a signal including meaningful data other than a value of '0' may be selectively adopted to easily implement frequency sampling without damaging the signal. The compression sensing unit 155 according to the present embodiment is capable of sampling at a relatively low speed without sampling the signal above the Nyquist rate based on the CS theory of restoring the original signal with a very small number of linear measurements of sparse signals (most signals with a value of 0).

The digital conversion unit 157 may convert the size of the signal sampled by the compression sensing unit 155 into a digital signal.

In this embodiment, the information converted by the digital conversion unit 157 may be compatible with a process or program that employs a digital method, and this may further improve the usability of the hybrid wave computer 1. The digital conversion unit 157 may transmit the binarized digital data to the artificial neural network 159 or the output module 19.

In addition, the digital conversion unit 157 may binarize and convert the signals transmitted according to the frequency characteristics. This may be utilized as a cornerstone for increasing the efficiency of the storage process of the storage module 17 in the future. In addition, data may be provided to the processor to selectively select basic data for machine learning.

The processor includes an artificial neural network algorithm so that it receives the magnitude of the signal of each frequency band of the original signal 3 outputted from the digital conversion unit 157 to generate output information through machine learning.

The processor may selectively receive the magnitude of the binary signal separated by the digital conversion unit 157 according to the frequency characteristic and through this, may perform machine learning based on various combinations of input values. The processor may transmit the product, which is calculated through the execution of the artificial neural network algorithm, to the output module 19. In addition, the processor may extract various information in real time by learning through the artificial neural network algorithm.

In the storage module 17, the frequency information binarized by the calculation module 15 may be stored as digital information.

The storage module 17 may store the frequency information of the original signal 3 that is electrically converted and is received from the calculation module 15. The storage module 17 may be provided in any form capable of storing electrically converted data. In one embodiment, the storage module 17 may be provided in a form including a device used in a digital computer such as a central processing unit (CPU), a random access memory (RAM) and a solid state drive (SSD) capable of storing electrically converted data using semiconductors. In another embodiment, the storage module 17 may be provided in a form including a hard disk drive (HDD) using magnetism, a magnetic tape, or the like.

The storage module 17 may divide the binarized frequency information by each frequency band and store it.

Figure 4:
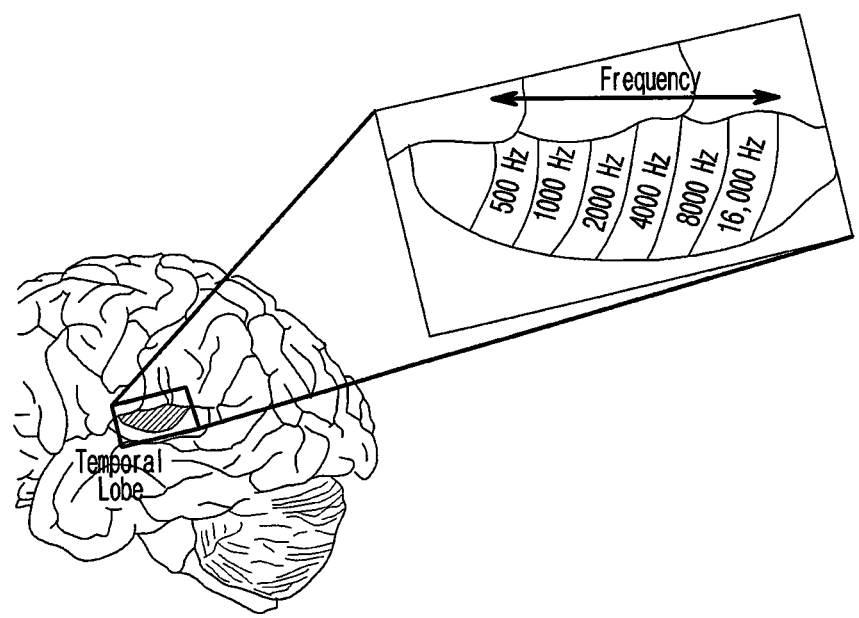
FIG. 4 shows an anatomical model diagram of a tonotopic map for explaining an embodiment of the present invention.

FIG. 4 shows an anatomical model diagram of a tonotopic map for explaining an embodiment of the present invention. Referring to FIG. 4, similar to the method in which the brain stores each sound information having different frequency characteristics at anatomically different locations, the storage module 17 stores, in a different space, the frequency-dependent data of the independently binarized original signal 3 in a digital conversion unit 157. This means that the computer form may simulate human form to perform a process, and in the hybrid wave computer 1 according to the present embodiment, the input module 13 may perform the function of the cochlea that divides sound into frequency bands, and the signal size is digitized and stored for each separated frequency band, and the structure of the storage module 17 and the data processing of the calculation module 15 may be implemented to be suitable for simulating the functions of the human sensory organs and brain.

The storage module 19 may store the frequency information of the original signal 3 that is electrically converted and is received from the calculation module 15. In one embodiment, the electrically converted frequency information may be outputted in a visually verifiable form. In another embodiment, the electrically converted frequency information may be outputted in an audibly verifiable form. As described above, the information outputted through the output module 19 is not limited to types or characteristics, and may be outputted in various ways so that it may be recognized by a user.

While the present invention is described in detail through representative embodiments, it will be understood by those skilled in the art that various changes in form and details may be made therein without departing from the spirit and scope of the invention as defined by the appended claims. Therefore, the scope of the present invention should not be limited to the embodiments described above, but should be defined by all variations or modifications derived from the appended claims and equivalents thereof, as well as the appended claims.

INDUSTRIAL APPLICABILITY

The present invention implements a physical virtual space full connection interfeel platform, which includes a sensor unit that responds to information with frequency components and an input module that is capable of calculating the wave based on the frequency component against discrete calculation using the information received from the sensor unit.

According to the present invention, by using the attenuation characteristics of the surface acoustic waves, the analog signal is separated into the input modules by frequency band, and the calculation necessary for interface is performed using the frequency band signal as the input value, so that information is calculated in the frequency band without a separate Fourier transform process. In addition, since the information of each frequency band signal is stored in the storage module as digital data, it may be linked with algorithms such as artificial neural networks.

Accordingly, the present invention is advantageous in that the analog input function is enhanced in addition to processing of existing user input or single sensor information, and information processing in which a human sense organ or brain is simulated may be performed.

The invention claimed is:

1. A hybrid wave computer that computes an inputted original signal as frequency information, the hybrid wave computer comprising:
    an input module including a substrate and a piezoelectric element, the input module configured to separate a frequency from the original signal, transmitted on the surface as a surface acoustic wave, by detecting a penetration depth of the surface acoustic wave based on an oscillation of the piezoelectric element;
    a calculation module including at least one vibration amplifier or vibration damper for receiving the frequency of the original signal separated in the input module and amplifying or attenuating a wave for each frequency band to calculate the inputted original signal in a frequency band; and
    a storage module configured to store binarized frequency information in the calculation module as digital information,
    wherein the original signal is interfaced in a form of waves.

2. The hybrid wave computer of claim 1, further comprising a sensor unit configured to oscillate the input module in response to an external environment.

3. The hybrid wave computer of claim 1, wherein the substrate is a piezoelectric substrate configured to receive the original signal and to convert the received original signal into the surface acoustic wave,
    wherein the piezoelectric substrate has a metal line formed on a surface thereof in a direction perpendicular to a direction in which the surface acoustic wave advances.

4. The hybrid wave computer of claim 3, wherein in the piezoelectric substrate, a plurality of the metal lines are arranged at regular intervals, and the metal lines are formed in an arrangement in which fixed ends are crossed in a vertical direction.

5. The hybrid wave computer of claim 4, wherein the input module further comprises an electrode port for outputting each separate frequency,
- wherein the electrode port is disposed in each area of the fixed ends.

6. The hybrid wave computer of claim 1, wherein the calculation module includes:
- a compression sensing unit configured to sample a magnitude of a signal for each separated frequency band of the original signal; and
- a digital conversion unit configured to binarize a magnitude of a signal sampled in the compression sensing unit to convert the binarized magnitude into a digital signal,
- wherein the compression sensing unit samples a signal with a value less than twice the highest frequency of the signal for each separated frequency band of the original signal.

7. The hybrid wave computer of claim 6, wherein the calculation module further comprises a processor having an artificial neural network algorithm embedded therein,
- wherein the processor receives a magnitude of a signal for each frequency band of the original signal outputted from the digital conversion unit and generates output information through machine learning.

8. The hybrid wave computer of claim 1, wherein the storage module divides the binarized frequency information by each frequency band and stores the divided binarized frequency information.

* * * * *